(12) United States Patent
Uchiyama et al.

(10) Patent No.: US 8,741,825 B2
(45) Date of Patent: Jun. 3, 2014

(54) HAIR WASHING COMPOSITION

(75) Inventors: Tomoko Uchiyama, Wakayama (JP); Hayato Yoshikawa, Wakayama (JP)

(73) Assignee: Kao Corporation, Tokyo (JP)

( * ) Notice: Subject to any disclaimer, the term of this patent is extended or adjusted under 35 U.S.C. 154(b) by 168 days.

(21) Appl. No.: 12/863,998

(22) PCT Filed: Mar. 3, 2009

(86) PCT No.: PCT/JP2009/000951
§ 371 (c)(1),
(2), (4) Date: Jul. 22, 2010

(87) PCT Pub. No.: WO2009/110223
PCT Pub. Date: Sep. 11, 2009

(65) Prior Publication Data
US 2010/0292116 A1 Nov. 18, 2010

(30) Foreign Application Priority Data

Mar. 4, 2008 (JP) ................. 2008-052907

(51) Int. Cl.
*C11D 1/14* (2006.01)
*C11D 1/29* (2006.01)
*C11D 1/90* (2006.01)
*C11D 1/94* (2006.01)
*C11D 3/26* (2006.01)

(52) U.S. Cl.
USPC ........... 510/123; 510/124; 510/125; 510/127; 510/130; 510/137; 510/138; 510/475; 510/492; 510/499; 510/504; 510/505; 510/506; 424/70.19; 424/70.21; 424/70.22; 424/70.27; 424/70.28

(58) Field of Classification Search
USPC ......... 510/123, 124, 125, 127, 130, 137, 138, 510/475, 492, 499, 504, 505, 506; 424/70.19, 70.21, 70.22, 70.27, 70.28
See application file for complete search history.

(56) References Cited

U.S. PATENT DOCUMENTS

| 5,811,087 A | 9/1998 | Möhring et al. |
| 6,069,216 A | 5/2000 | Iwasaki et al. |
| 2004/0157984 A1 | 8/2004 | Sakai et al. |

FOREIGN PATENT DOCUMENTS

| JP | 4-108724 | 4/1992 |
| JP | 6-41580 | 2/1994 |
| JP | 9-110652 | 4/1997 |
| JP | 11 71435 | 3/1999 |
| JP | 2000 144183 | 5/2000 |
| JP | 2000 144184 | 5/2000 |
| JP | 2000-144185 | 5/2000 |
| JP | 2000 144185 | 5/2000 |
| JP | 2004-217644 | 8/2004 |
| JP | 2004 307700 | 11/2004 |
| JP | 2005 336387 | 12/2005 |
| JP | 2006 282662 | 10/2006 |

*Primary Examiner* — Gregory R Delcotto
(74) *Attorney, Agent, or Firm* — Oblon, Spivak, McClelland, Maier & Neustadt, L.L.P.

(57) ABSTRACT

To provide a cleansing composition showing excellent properties during cleansing and rinsing while satisfying foam performance.

The hair cleansing composition according to the invention contains the following ingredients (A), (B), (C), and (D) at a weight ratio of Ingredient (A) to Ingredient (B) [(A)/(B)] is of from 0.1 to 1.2 and at a weight ratio of Ingredient (A) to Ingredient (C) [(A)/(C)] of from 0.1 to 1.2:

(A) an ether carboxylate surfactant,
(B) an ether sulfate surfactant,
(C) a betaine amphoteric surfactant,
(D) a cationic-group containing copolymer obtained by the copolymerization of a monomer mixture containing three monomers.

18 Claims, No Drawings

HAIR WASHING COMPOSITION

CROSS REFERENCE TO RELATED APPLICATION

This application is a 371 of PCT/JP09/000951, filed on Mar. 3, 2009, and claims priority to Japanese Patent Application No. 2008-052907, filed on Mar. 4, 2008.

FIELD OF THE INVENTION

The present invention relates to a hair cleansing composition.

BACKGROUND OF THE INVENTION

Alkyl sulfate, polyoxyethylene alkyl ether sulfate, polyoxyethylene alkyl ether acetate, a succinic acid surfactant or an amino acid surfactant is conventionally used as a primary surfactant for a hair cleansing composition. As well, incorporating a cationic polymer into a cleansing composition is known as a way to improve the finger combability through the hair during shampooing/rinsing.

Patent Document 1 discloses a hair cleansing composition comprising (A) a copolymer which has a cationic group and a crosslinked structure in a molecular thereof, and which also carries a feature such that its 0.5 wt. % hydrogel satisfies the following equations: $0.3 \leq \eta 1 \leq 20$ (Pa·sec), $0.01 \leq \eta 2 \leq 5$ (Pa·sec), and $\eta 1 > \eta 2$, wherein $\eta 1$ means a viscosity at a shear rate of 1 sec$^{-1}$ and $\eta 2$ means a viscosity at a shear rate of 10 sec$^{-1}$, each at 25° C., and (B) an anionic surfactant. According to its disclosure, the composition is nice to the touch and excellent in spreadability during application, has a good foamability, is superior in hair sensation during cleansing or after drying, and even more has a high conditioning effect after cleansing.

Patent Document 2 discloses a novel cleansing and conditioning composition containing (A) at least one sulfate or sulfonate anionic surfactant, (B) at least one carboxylic acid anionic surfactant other than the surfactant described in (A) and selected from polyoxyalkylenated ($C_6$-$C_{24}$) alkyl ether carboxylic acids, polyoxyalkylenated ($C_6$-$C_{24}$) alkyl aryl ether carboxylic acids or salts thereof, and polyoxyalkylenated ($C_6$-$C_{24}$) alkylamido ether carboxylic acids or salts thereof, (C) at least one amphoteric surfactant, and (D) at least one water-insoluble carboxylic ester.

Patent Document 3 discloses a cleansing composition containing the following three ingredients (A), (B) and (C): (A) an ether carboxylic acid surfactant represented by the formula (1), (B) a glyceryl ether having an alkyl or alkenyl group with from 4 to 12 carbon atoms, and (C) a cationic-group containing copolymer. The composition is described to be less irritating to the skin, has excellent foamability and foam quality, and provide a good sensation during cleansing and rinsing and after drying.

However, even such cleansing compositions taking advantage of the conventional technologies are still not enough to satisfy both of the foam performance and function needed for a hair cleansing composition simultaneously.
Patent Document 1: JP-A-2000-144184
Patent Document 2: JP-A-2006-282662
Patent Document 3: JP-A-2005-336387

DISCLOSURE OF THE INVENTION

The present invention provides a hair cleansing composition containing the following ingredients (A), (B), (C) and (D), wherein an ingredient (A)/ingredient (B) weight ratio [(A)/(B)] is from 0.1 to 1.2 and an ingredient (A)/ingredient (C) weight ratio [(A)/(C)] is from 0.1 to 1.2:

(A) an ether carboxylate surfactant,
(B) an ether sulfate surfactant,
(C) a betaine amphoteric surfactant,
(D) a cationic-group containing copolymer obtained by the copolymerization of a monomer mixture containing the following monomers (a1), (a2), and (a3):

(a1) at least one hydrophilic nonionic-group containing vinyl monomer represented by the following formula (I) or (II):

wherein $R^1$ represents a hydrogen atom or a methyl group, $R^2$ represents a hydrogen atom or a linear or branched alkyl or alkenyl group having from 1 to 4 carbon atoms, and $R^3$ represents a linear or branched alkyl or alkenyl group having from 1 to 4 carbon atoms;

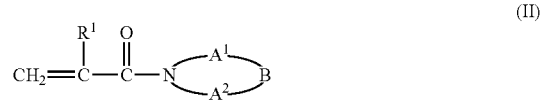

wherein $R^1$ has the same meaning as described above, $A^1$ and $A^2$ are the same or different and each represents a group represented by the formula: —(CH$_2$)$_n$— (n stands for an integer from 2 to 6), and B represents a group —O— or —CH$_2$—, (a2) at least one cationic-group containing vinyl monomer represented by the following formula (III) or (IV):

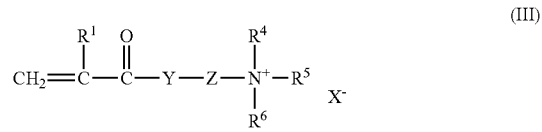

wherein $R^1$ has the same meaning as described above, $R^4$ and $R^5$ are the same or different and each represents an alkyl or alkenyl group having from 1 to 4 carbon atoms, $R^6$ represents a hydrogen atom or an alkyl group having from 1 to 4 carbon atoms, Y represents a group —O—, —NH—, —CH$_2$—, or —O—CH$_2$CH(OH)—, Z represents a linear or branched alkylene group having from 1 to 4 carbon atoms (with the proviso that when Y is —CH$_2$—, the number of carbon atoms is from 0 to 3), and X represents a conjugate base of an acid;

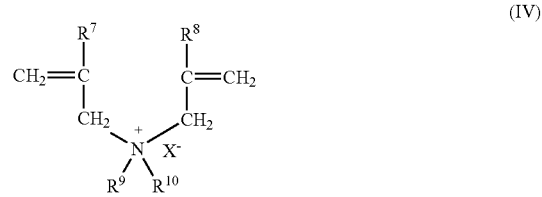

wherein $R^7$ and $R^8$ are the same or different and each represents a hydrogen atom or a methyl group, $R^9$ and $R^{10}$ are the same or different and each represents a hydrogen atom or an alkyl group having from 1 to 4 carbon atoms, and X has the same meaning as described above, and (a3) a crosslinkable monomer having two or more reactive unsaturated groups.

The present invention also provides use of a composition containing the above ingredients (A), (B), (C), and (D), wherein an ingredient (A)/ingredient (B) weight ratio [(A)/(B)] is from 0.1 to 1.2 and an ingredient (A)/ingredient (C) weight ratio [(A)/(C)] is from 0.1 to 1.2, as a hair cleansing agent.

The present invention further provides a method for cleansing the hair, which includes using, for the hair, a composition containing the ingredients (A), (B), (C) and (D), wherein an ingredient (A)/ingredient (B) weight ratio [(A)/(B)] is from 0.1 to 1.2 and an ingredient (A)/ingredient (C) weight ratio [(A)/(C)] is from 0.1 to 1.2.

DETAILED DESCRIPTION OF THE INVENTION

An object of the invention is to provide a cleansing composition which is excellent in hair sensation during cleansing and rinsing, especially excellent in finger combability, and is superior in softness, while satisfying foam performance.

The hair cleansing composition of the invention is excellent in hair sensation during cleansing and rinsing, while satisfying the foam performance needed when the hair is shampooed with it.

The present invention was completed based on the finding that a cleansing composition containing the above ingredients (A) to (D) at a predetermined ratio provides an excellent sensation to the hair during cleansing and rinsing, while satisfying foam performance.

This is because it becomes easier for a structural composite (hereinafter "composite" for simplicity), which capable of improving finger combability and softness while satisfying foam performance, to precipitate owing to the use of a cationic-group containing copolymer as ingredient (D) and a surfactant composition containing ingredients (A), (B), and (C) at a predetermined ratio when subjected to a dilution step during cleansing, and then to a dilution step during rinsing.

Moreover, the hair cleansing composition of the invention including silicone has the ability to produce an excellent sensation in softness or finger combability not only during cleansing and rinsing but also when the hair is wet or dry. This is presumably because silicone is incorporated in the composite during cleansing or rinsing to improve the performance of the composite and in addition, heighten the residual property of silicone on the hair.

The constitution of the invention will hereinafter be described in detail.

The ether carboxylate surfactant as ingredient (A) is thought to be a principal ingredient for developing, mainly through an interaction with ingredient (D), the performance of the composite that relates to improvement of finger combability and softness. Ingredient (A) is not particularly limited, but is preferably a surfactant represented by the following formula (4) or (5).

wherein $R^{11}$ represents an alkyl or alkenyl group which may contain a linear or branched hydroxyl group having from 5 to 21 carbon atoms, $Z^1$ represents —O— or —CONH—, $A^1$ represents an alkylene group having 2 or 3 carbon atoms, $X^1$ represents a hydrogen atom, an alkali metal, an alkaline earth metal, ammonium, or an organic ammonium, $Y^1$ represents an alkylene group having from 1 to 3 carbon atoms, and n stands for an average addition molar number and is from 2 to 15. When $X^1$ represents an alkaline earth metal, the molar ratio becomes 1/2 relative to the surfactant. This will equally apply hereinafter.

In the formula (4), when $Z^1$ represents —O—, $R^{11}$ is preferably the group having from 12 to 16 carbon atoms. When $Z^1$ represents —CONH—, $R^{11}$ is preferably the group having from 11 to 15 carbon atoms. $A^1$ represents an ethylene or propylene group, with an ethylene group being preferred.

The average addition molar number n is preferably from 2 to 11, more preferably from 4 to 10 from the standpoint of a foam volume and hair sensation during cleansing and rinsing. It is preferably from 2 to 6 from the viewpoint of a foam volume, while it is preferably from 6 to 11 from the standpoint of finger combability and softness during cleansing and rinsing. It is also preferred to use, in combination, two or more ether carboxylate surfactants different in the average addition molar number.

With regard to $X^1$, examples of the alkali metal include lithium, sodium, and potassium; those of the alkaline earth metal include magnesium and calcium; those of the organic ammonium include alkanolammoniums having preferably from 2 to 9 carbon atoms such as triethanolammonium; alkylammoniums having preferably from 1 to 9 carbon atoms such as trimethylammonium; and basic amino acid cations such as lysine cation and arginine cation. Of these, alkali metals such as sodium and potassium are preferred. $Y^1$ is preferably a methylene group having one carbon atom.

Formula (5):

(5)

wherein $R^{12}$ represents a linear or branched alkyl or alkenyl group having from 4 to 34 carbon atoms, at least one of $X^2$ and $X^3$ represents —$CH_2COOM^1$ and the other one may represent a hydrogen atom, and $M^1$ represents a hydrogen atom, an alkali metal, an alkaline earth metal, ammonium, or an organic ammonium.

In the formula (5), $R^{12}$ represents the group having preferably having 8 to 25 carbon atoms, more preferably from 8 to 18 carbon atoms. $X^2$ and $X^3$ both represent —$CH_2COOM^1$ or at least one of them represents —$CH_2COOM^1$ and the other one represents a hydrogen atom. Preferred examples of $M^1$ are similar to the above examples of $X^1$.

Commercially available ether carboxylate surfactants are, for example, "BEAULIGHT" (trade name), product of Sanyo Chemical and "KAOAKYPO RLM" Series (trade name), product of Kao Corporation. Ether carboxylic acids described in JP-A-06-316546 are also usable. Specific examples include polyoxyethylene (average addition molar number: from 4 to 10) decyl ether acetates, polyoxyethylene (average addition molar number: from 4 to 10) lauryl ether acetates, polyoxyethylene (average addition molar number: from 4 to 10) myristyl ether acetates, and polyoxyethylene (average addition molar number: from 4 to 10) cetyl ether acetates. Examples of salts include sodium, potassium, ammonium, triethanolammonium salts.

The ether sulfate surfactant as ingredient (B) is presumed to improve mainly the foam performance and at the same time, facilitates precipitation of the structural composite together with ingredient (C). Ingredient (B) is not particularly limited, but is preferably represented by the following formula (6):

wherein $R^{13}$ represents an alkyl or alkenyl group having from 6 to 22 carbon atoms, p means an average addition molar number and is from 0.5 to 5, and $M^2$ represents a hydrogen atom, an alkali metal, an alkaline earth metal, ammonium, or an organic ammonium.

In the above formula, $R^{13}$ is preferably the group having from 10 to 18 carbon atoms from the standpoint of foamability, and p is preferably from 0.5 to 3 from the standpoint of foamability. Preferred examples of $M^2$ are similar to those of $X^1$.

Commercially available ether sulfate surfactants are for example "EMAL" series (trade name), product of Kao Corporation. Specific examples include polyoxyethylene (average addition molar number: from 0.5 to 3) decyl ether sulfates, polyoxyethylene (average addition molar number: from 0.5 to 3) lauryl ether sulfates, polyoxyethylene (average addition molar number: from 0.5 to 3) myristyl ether sulfates, and polyoxyethylene (average addition molar number: from 0.5 to 3) cetyl ether sulfates. Examples of their salts include sodium, potassium, ammonium, and triethanolammonium salts.

The betaine amphoteric surfactant as Ingredient (C) is presumed to have mainly foam enhancing properties and at the same time facilitate precipitation of the structural composite together with ingredient (B). Examples of ingredient (C) include carbobetaine and amidocarbobetaine surfactants (hereinafter referred to as "carbobetaine" collectively), sulfobetaine and amidosulfobetaine surfactants (hereinafter referred to as "sulfobetaine", collectively), and imidazolinium betaine and phosphobetaine surfactants.

Specific examples include carbobetaines and amidocarbobetaines represented by the following formulas (B-2a) and (B-2b), sulfobetaines and amidosulfobetaines represented by the following formulas (B-2c) and (B-2d), and imidazolinium betaines represented by the following formula (B-2e) or (B-2f).

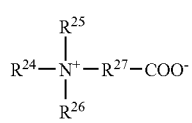

(B-2a)

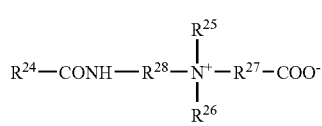

(B-2b)

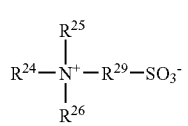

(B-2c)

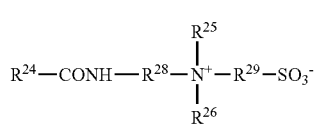

(B-2d)

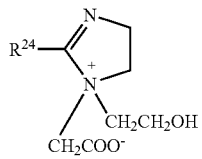

(B-2e)

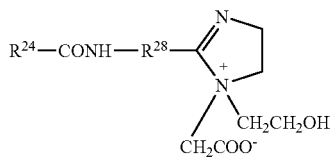

(B-2f)

In the above formulas, $R^{24}$ represents an alkyl or alkenyl group having from 6 to 22 carbon atoms, $R^{25}$ and $R^{26}$ each represents an alkyl or hydroxyalkyl group having from 1 to 5 carbon atoms, $R^{27}$ represents an alkylene or hydroxyalkylene group having from 1 to 6 carbon atoms, $R^{28}$ represents a single bond or an alkylene group having from 1 to 5 carbon atoms, and $R^{29}$ represents an alkylene or hydroxyalkylene group having from 1 to 5 carbon atoms.

Of the various betaines represented by the formulas (B-2a) to (B-2f), those having as $R^{24}$ an alkyl group with from 8 to 16 carbon atoms, as $R^{25}$ and $R^{26}$ a methyl group, as $R^{27}$ to $R^{29}$ an alkylene group with from 1 to 5 carbon atoms are preferred. Specific examples include alkyl dimethylaminocarbobetaines, alkyl amidoalkylenedimethylaminocarbobetaines, alkyl dimethylaminohydroxysulfobetaines, alkyl amidoalkylenedimethylaminosulfobetaines, alkyl hydroxyethyl imidazolinium betaines, and alkyl amidohydroxyethyl imidazolinium betaines. More specifically, lauramidopropyl betaine, cocamidopropyl betaine, and lauryldimethylhydroxysulfobetaine are preferred.

Of these, at least one amphoteric surfactant selected from the group consisting of carbobetaines and sulfobetaines is preferred from the standpoint of foam performance and hair sensation during cleansing and rinsing. It is more preferred to use them in combination. The carbobetaine and the sulfobetaine are used preferably at a weight ratio (carbobetaine/sulfobetaine) from 1/5 to 5/1, more preferably from 1/3 to 3/1 from the standpoint of foam performance and hair sensation during cleansing and rinsing.

Ingredient (D) to be used in the invention is a cationic-group containing copolymer available by polymerization of the above monomers (a1), (a2), and (a3) as essential constituent monomers.

Monomer (a1) is at least one hydrophilic nonionic-group containing vinyl monomer represented by the following formula (I) or (II):

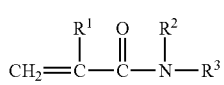

(I)

wherein $R^1$ represents a hydrogen atom or a methyl group, $R^2$ represents a hydrogen atom or a linear or branched alkyl or alkenyl group having from 1 to 4 carbon atoms, and $R^3$ represents a linear or branched alkyl or alkenyl group having from 1 to 4 carbon atoms.

(II)

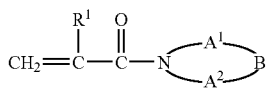

wherein $R^1$ has the same meaning as described above, $A^1$ and $A^2$ are the same or different and each is a group represented by the formula: —$(CH_2)_n$— (n stands for an integer from 2 to 6), and B represents a group —O— or —$CH_2$—.

In the formula (I), $R^2$ is preferably a linear or branched alkyl or alkenyl group having from 1 to 4 carbon atoms from the standpoint of finger combability and softness during rinsing. Preferred groups of $R^2$ and $R^3$ are the same or different and include a methyl group, an ethyl group, a propyl group, an isopropyl group, a butyl group, an isobutyl group, or a t-butyl group.

Examples of the hydrophilic nonionic-group containing vinyl monomer represented by the formula (I) include N-methyl(meth)acrylamide, N,N-dimethyl(meth)acrylamide, N,N-diethyl(meth)acrylamide, N-n-propyl(meth)acrylamide, N-isopropyl(meth)acrylamide, N-t-butyl(meth)acrylamide, and N-isobutyl(meth)acrylamide. The hydrophilic nonionic-group containing vinyl monomer represented by the formula (II) is, for example, N-(meth)acrolylmorpholine, but N,N-(di-substituted)acrylamides provide good feeling upon use. Use of N,N-dimethyl(meth)acrylamide or N,N-diethyl (meth)acrylamide is more preferred.

Monomer (a2) is at least one cationic-group containing vinyl monomer represented by the following formula (III) or (IV):

(III)

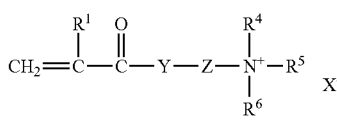

wherein $R^1$ has the same meaning as described above, $R^4$ and $R^5$ are the same or different and each represents an alkyl or alkenyl group having from 1 to 4 carbon atoms, $R^6$ represents a hydrogen atom or an alkyl group having from 1 to 4 carbon atoms, Y represents a group —O—, —NH—, —$CH_2$—, or —O—$CH_2CH(OH)$—, Z represents a linear or branched alkylene group having from 1 to 4 carbon atoms (with the proviso that when Y is —$CH_2$—, the number of carbon atoms is from 0 to 3), and X represents a conjugate base of an acid, (IV)

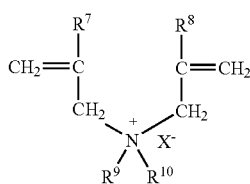

wherein $R^7$ and $R^8$ are the same or different and each represents a hydrogen atom or a methyl group, $R^9$ and $R^{10}$ are the same or different and each represents a hydrogen atom or an alkyl group having from 1 to 4 carbon atoms, and X has the same meaning as described above.

$R^4$, $R^5$, $R^6$, $R^9$, and $R^{10}$ are preferably the same or different and each represents a methyl group, an ethyl group, a propyl group, an isopropyl group, a butyl group, an isobutyl group, and a t-butyl group.

X is preferably a halogen atom or an alkyl sulfate group having from 1 to 4 carbon atoms.

Preferred examples of an acid to obtain a salt of the monomer (III) or (IV) include hydrochloric acid, sulfuric acid, acetic acid, citric acid, succinic acid, adipic acid, and sulfamic acid. Preferred examples of a quaternizing agent to obtain a quaternary ammonium salt include alkyl halides such as methyl chloride and methyl iodide, and diethyl sulfate and di-n-propyl sulfate.

Examples of Monomer (a2) include quaternary ammonium salts obtained by quaternizing, with above-mentioned quaternizing agent, dimethylaminoethyl(meth)acrylate, diethylaminoethyl(meth)acrylate, dimethylaminopropyl (meth)acrylamide, or diethylaminopropyl(meth)acrylamide, and dimethyldiallyl ammonium chloride.

Monomer (a3) is a crosslinkable monomer having two or more reactive unsaturated groups. Specific examples include (1) (meth)acrylate compounds of a polyhydric alcohol such as ethylene glycol di(meth)acrylate, diethylene glycol di(meth)acrylate, polyethylene glycol di(meth)acrylate, propylene glycol di(meth)acrylate, dipropylene glycol di(meth) acrylate, polypropylene glycol di(meth)acrylate, 1,2-butylene glycol di(meth)acrylate, 1,3-butylene glycol di(meth) acrylate, neopentyl glycol di(meth)acrylate, glycerin di(meth)acrylate, glycerin tri(meth)acrylate, trimethylolpropane tri(meth)acrylate, and pentaerythritol tetra(meth)acrylate; (2) divinyl compounds such as divinylbenzene, divinylether, and divinylethylene urea; and (3) polyallyl compounds such as diallyl phthalate, diallyl maleate, dilallylamine, triallylamine, triallylammonium salt, allyl-etherified pentaerythritol, and allyl-etherified sucrose having, in the molecule thereof, at least two allyl ether units. Preferred are (1) (meth)acrylate compounds of a polyhydric alcohol and at least one selected from ethylene glycol di(meth)acrylate and polyethylene glycol di(meth)acrylate is even more preferred.

Monomer (a1) and Monomer (a2) are added at an (a1)/(a2) molar ratio of preferably from 2/98 to 98/2, more preferably from 50/50 to 95/5, even more preferably from 60/40 to 93/7 from the standpoint of foamability, tangle-free hair during shampooing, and rinsability.

Monomer (a3) is added in an amount of from 0.002 to 5 wt. % based on a total amount of the monomers from the standpoint of foamability, tangle-free hair during shampooing, suitability for scalp massage, and rinsability. It is more preferably from 0.002 to 0.5 wt. %, even more preferably from 0.002 to 0.08 wt. % from the standpoint of hair sensation during rinsing for providing the hair with softness and good slip.

A preparation process of the copolymer of ingredient (D) is described in Paragraph [0041] to [0045] and Examples of JP-A-11-71435.

Ingredient (D) has a cationic charge density of preferably from 0.3 to 2.5 meq/g, more preferably from 0.3 to 2 meq/g, even more preferably from 0.5 to 1.5 meq/g from the standpoint of finger combability and softness during cleansing and rinsing.

The cationic charge density can be determined from the following equation based on a charged cation monomer amount of a polymer.

Cationic charge density of polymer (meq/g)=(weight of $a2$)×1000/[(total weight of $a1+a2+a3$)×(molecular weight of $a2$)]

Ingredient (D), in the form of a 0.5% hydrogel, preferably satisfies the following equations: $0.3 \leq \eta1 \leq 20$ (Pa·sec), $0.01 \leq \eta2 \leq 5$ (Pa·sec), and $\eta1 > \eta2$, wherein η1 is a viscosity at a shear rate of 1 sec$^{-1}$ and η2 is a viscosity at a shear rate of 10 sec$^{-1}$, each at 25° C.

When the viscosity behavior falls within the above range, feeling upon use, more specifically, excellent foamability, tangle-free hair during shampooing, and rinsability can be achieved. In particular, when ingredient (D) satisfies $0.4 \leq \eta 1 \leq 10$ (Pa·sec) and $0.5 \leq \eta 2 \leq 3$ (Pa·sec), feeling upon use is improved further.

When ingredient (D), in the form of a 0.5% hydrogel, satisfies the following equations under the conditions of 25° C. and a strain frequency of 6.28 rad/sec: $1 \leq \epsilon 1 \leq 300$ (N/m$^2$) and tan $\delta 1 \leq 2$ and at the same time, $0.01 \leq \epsilon 2 \leq 30$ (N/m$^2$) and tan $\delta 2 \geq 1$ wherein $\epsilon 1$ is a complex modulus and tan $\delta 1$ is a loss tangent each at strain 1%, and $\epsilon 2$ is a complex modulus and tan $\delta 2$ is a loss tangent each at strain 500%, a hair cleansing composition with a more preferable hair sensation can be obtained. As a range of the loss tangent of ingredient (D) to be satisfied becomes narrower: tan $\delta 1 \leq 1.5$ and then: tan $\delta 1 \leq 1.0$, a hair cleansing composition having a even more preferable sensation can be obtained.

The $\eta 1$ and $\eta 2$ are measured in the following manner:
Specimen 1: A 0.5% hydrogel obtained by adding a powder sample (having an average particle size not greater than 50 µm) to ion exchanged water and retaining the mixture at 50° C. for half a day.
Measuring apparatus: "Rotovisco RV-20", trade name; a viscometer manufactured by HAAKE
Measurement conditions: Measuring head: M10, coaxial two-wall cylindrical type rotor, measuring temperature: 25° C., and sample amount: 15 ml.
Shear rate: Increased from 0 sec$^{-1}$ to 15 sec$^{-1}$ over two minutes.
The number of data: Obtained at 60 points within the above range of the shear rate.
Computation method: Calculated from the above measured values by using a program of Rotation Version 2.8.

The $\delta 1$, $\delta 2$, $\epsilon 1$, and $\epsilon 2$ are measured in the following manner.
Specimen: The same as Specimen 1
Measuring apparatus: "Fluids Spectrometer RFS-II", trade name; product of Rheometrics.
Measuring conditions: Dynamic Strain Sweep mode
Cone plate: Diameter: 50 mm, gap: 0.05 mm, angle: 0.04 rad, strain frequency: 6.2 rad/sec, strain: from 0.5 to 500%.
Measuring temperature: 25° C.

Ingredient (D) is preferably polymer particles from the standpoint of improving finger combability and softness during cleansing and rinsing. Its average particle size (median particle size based on volume) is preferably from 0.1 to 10 µm, more preferably from 0.5 to 5 µm, even more preferably from 1 to 4 µm from the above standpoint.

When Ingredient (D) has a particle size within the above range, an adequate amount of silicone as Ingredient (E) can be incorporated in the structural complex and the resulting hair cleansing composition is excellent in finger combability, slip, and softness after drying.

As the average particle size, a median particle size based on volume (D50) is measured by dispersing the powder of ingredient (D) in cyclohexane by using an apparatus to give a measurable arbitrary concentration (around 10 wt. %), adding several drops of the resulting polymer dispersion to a measurement solvent (cyclohexane) and retaining it for one minute.
Measuring apparatus: "Laser diffraction particle size analyzer LS230" (with a small volume module), trade name; product of Beckman Coulter.

The content of Ingredient (A) in the cleansing composition of the invention is preferably from 1 to 10 wt. %, more preferably from 1 to 8 wt. %, even more preferably from 1.8 to 7 wt. % (in terms of an acid percentage, which will equally apply hereinafter) from the standpoint of softness during cleansing and finger combability during rinsing both provided through an interaction with Ingredient (D). The weight ratio of Ingredient (D) to Ingredient (A) [Ingredient (D)/Ingredient (A)] in the cleansing composition of the invention should be raised to a certain level in order to determine the performance of the structural complex. It is preferably from 0.05 to 0.3, more preferably from 0.06 to 0.25, even more preferably from 0.07 to 0.2 from the standpoint of softness during cleansing and finger combability during rinsing.

The content of Ingredient (B) in the cleansing composition of the invention is preferably from 1 to 20 wt. %, more preferably from 2 to 15 wt. %, even more preferably from 3.5 to 13 wt. % from the standpoint of a foam performance and also from the standpoint of facilitating precipitation of the structural complex together with Ingredient (C) through an interaction with Ingredient (D).

The content of Ingredient (C) in the cleansing composition of the invention is preferably from 2 to 20 wt. %, more preferably from 2 to 15 wt. %, even more preferably from 3 to 13 wt. % from the standpoint of a foam enhancing performance and also from the standpoint of facilitating precipitation of the structural complex together with Ingredient (B) through an interaction with Ingredient (D) and improving the softness during cleansing. The weight ratio of Ingredient (D) to Ingredient (C) [Ingredient (D)/Ingredient (C)] in the cleansing composition of the invention is preferably from 0.02 to 0.25, more preferably from 0.03 to 0.2, even more preferably from 0.03 to 0.15 from the above standpoint.

The total content of Ingredient (A), Ingredient (B), and Ingredient (C) in the cleansing composition of the invention is preferably from 3 to 30 wt. %, more preferably from 5 to 25 wt. %, even more preferably from 5 to 20 wt. % from the standpoint of a sufficient foam performance and finger combability and softness during cleansing and rinsing. As Ingredient (D), one or more of the above copolymers can be used. The content of it in the cleansing composition of the invention is preferably from 0.01 to 3 wt. %, more preferably from 0.05 to 2 wt. %, even more preferably from 0.1 to 1 wt. % from the standpoint of finger combability and softness during cleansing and rinsing.

The weight ratio of Ingredient (A) to Ingredient (C) [(A)/(C)] in the cleansing composition of the invention is from 0.1 to 1.2, preferably from 0.15 to 1, more preferably from 0.2 to 0.8. The weight ratios less than 0.1 may deteriorate finger combability and softness during cleansing and rinsing which will be imparted through an interaction with Ingredient (D). The weight ratios exceeding 1.2 may deteriorate the foam performance.

The weight ratio of Ingredient (B) to Ingredient (C) [(B)/(C)] in the cleansing composition of the present invention is preferably from 0.1 to 6, more preferably from 0.2 to 5, even more preferably from 0.3 to 3 from the standpoint of a foam performance and also from the viewpoint of facilitating precipitation of the structural complex through an interaction among Ingredients (B), (C), and (D) and improving the finger combability and softness during cleansing and rinsing.

The weight ratio of Ingredient (A) to Ingredient (B) [(A)/(B)] in the cleansing composition of the invention is preferably from 0.1 to 1.2, more preferably from 0.15 to 1, even more preferably from 0.2 to 0.8. The weight ratios less than 0.1 may deteriorate finger combability and softness during cleansing and rinsing which will be imparted through an interaction with Ingredient (D). The weight ratios exceeding 1.2 may deteriorate the foam performance.

The weight ratio of the content of Ingredient (A) to the total content of Ingredients (A), (B), and (C) [Ingredient (A)/[Ingredient (A)+Ingredient (B)+Ingredient (C)] in the cleansing composition of the invention is preferably from 0.08 to 0.37, more preferably from 0.1 to 0.3, even more preferably from 0.1 to 0.25 mainly from the viewpoint of balance between improving finger combability and softness during cleansing and rinsing, and the foam performance.

The weight ratio of the content of Ingredient (B) to the total content of Ingredients (A), (B), and (C) [Ingredient (B)/[Ingredient (A)+Ingredient (B)+Ingredient (C)] is preferably from 0.1 to 0.8, more preferably from 0.2 to 0.7, even more preferably from 0.2 to 0.6 mainly from the viewpoint of balance between improving the foam performance, and the finger combability and softness during cleansing and rinsing.

The weight ratio of the content of Ingredient (C) to the total content of Ingredients (A), (B), and (C) [Ingredient (C)/[Ingredient (A)+Ingredient (B)+Ingredient (C)] is preferably from 0.1 to 0.8, more preferably from 0.2 to 0.8, even more preferably from 0.2 to 0.7 from the viewpoint of the balance between the foam performance, and the finger combability and softness during cleansing and rinsing.

The weight ratio of the content of Ingredient (D) to the total content of Ingredients (A), (B), and (C) [Ingredient (D)/[Ingredient (A)+Ingredient (B)+Ingredient (C)] in the cleansing composition is preferably from 0.005 to 0.1, more preferably from 0.007 to 0.05 from the viewpoint of precipitating the structural complex.

In the hair cleansing composition of the invention, the structural complex can, through an interaction between the cationic-group containing copolymer as Ingredient (D) and a surfactant composition containing Ingredients (A), (B), and (C), leave an oil ingredient such as silicone and perfume, or a humectant such as ceramide on the hair efficiently during rinsing.

The precipitation amount of the structural complex of the hair cleansing composition of the invention can be determined using a model cleansing composition obtained by setting a surfactant concentration at a certain value and removing ingredients having an influence on the measurement of the precipitation amount.

Described specifically, it can be determined from a turbidity found in accordance with the following equation (1) from a transmittance T(%) (600 nm) of a cleansing composition, which has been prepared in Step 1, at the time of dilution in Step 2:

$$\text{Turbidity}(\%) = 100 - T(\%) \quad (1)$$

Step 1: A step of preparing a cleansing composition to give a total content of Ingredient (A) to (C) of 15 wt. % while keeping the above composition ratio of Ingredients (A), (B), (C), and (D), with the proviso that the cleansing composition contains, as ingredients other than Ingredients (A) to (D), only 1 wt. % of NaCl, purified water, and if necessary, a pH regulator and has a pH (at 20° C.) adjusted to 6.0.

Step 2: a step of diluting 1 g of the cleansing composition obtained in Step 1 with 7 g of hard water having water hardness of 4°.

In Step 1, the cleansing composition is prepared to give a total content of Ingredients (A) to (C) of 15 wt. %, while keeping the above composition ratio of Ingredients (A) to (D). In order to measure the transmittance at the time of dilution, the cleansing composition contains, as ingredients other than Ingredients (A) to (D), only 1 wt. % of NaCl, purified water, and if necessary, a pH regulator. It is prepared so as not to contain surfactants other than Ingredients (A) to (C), a polymer other than Ingredient (D), silicone, and a pearling agent.

In order to adjust the pH (at 20° C.) of the composition to 6.0, NaOH or HCl is added as a pH regulator if necessary.

In Step 2, the structural complex is precipitated by adding 7 g of hard water having water hardness of 4° to 1 g of the cleansing composition obtained in Step 1 for dilution. Within five minutes after dilution, the transmittance is measured. For the measurement of the transmittance, a glass cell having a length of 1 cm is employed.

The turbidity (%) is preferably 10 or greater, more preferably from 10 to 60, even more preferably from 10 to 50 in order to give, to the hair, an excellent hair sensation in finger combability and softness during cleansing and rinsing.

The complex available from predetermined amounts of the surfactants as Ingredients (A) to (C) and the cationic-group containing copolymer as Ingredient (D) gives an excellent sensation to the hair during cleansing and rinsing.

In the invention, it is preferred to add silicone as Ingredient (E) from the standpoint of imparting to the hair an excellent sensation in softness and finger combability during wetting or after drying.

Any silicone or silicone derivative is usable as Ingredient (E) insofar as it is used ordinarily for cosmetics. Examples include dimethicone, dimethiconol, polyether modified silicone, polyglycerin modified silicone, branched (poly)glycerol modified silicone, glyceryl ether modified silicone, amino modified silicone, aminopolyether modified silicone, amidoalkyl modified silicone, aminoglycol modified silicone, oxazoline modified silicone, acrylic/aminosilicone copolymer, phenyl modified silicone, aminophenyl modified silicone, polyamide modified silicone, alkyl modified silicone, silicone elastomer (powder), and crosslinked polymer coated with modified silicone (powder).

As commercially available silicone or silicone derivatives, those put on the market from silicone manufacturers such as Shin-Etsu Chemical and Dow Corning Toray and listed in the brochures such as "Silicones for cosmetics" or "Silicones for personal care" can also be used.

Silicones described in JP-A-04-108795 and JPA-2004-339244 are also usable.

As Ingredient (E), one or more of those listed above can be used. It is incorporated in the hair cleansing composition of the invention in an amount of preferably from 0.5 to 5 wt. %, more preferably from 1 to 3 wt. %. A weight ratio of Ingredient (D) to Ingredient (E) [(D)/(E)] is preferably from 1/20 to 1/1, more preferably for 1/10 to 1/2 from the standpoint of facilitating incorporation of Ingredient (E) in the complex of the cationic-group containing copolymer (D) and the surfactants and imparting, to the hair, an excellent sensation in softness and finger combability during wetting or after drying.

The hair cleansing composition of the invention can contain, in addition to the above essential ingredients, another ingredient ordinarily employed for cleansing agents without disturbing the advantage of the invention, depending on the using purpose. Examples include anionic surfactants other than Ingredients (A) and (B) such as alkyl sulfates, succinic acid surfactants, and amino acid surfactants; nonionic surfactants such as polyoxyalkylene alkyl ethers, alkyl glyceryl ethers, fatty acid alkanolamides, and alkyl polyglucosides; cationic surfactants such as alkyltrimethylammonium chloride and dialkyldimethylammonium chloride; cationic polymers other than Ingredient (D) such as cationic polysaccharide, cationic polypeptide, acrylamide/acrylic acid/dimethyldiallylammonium chloride copolymer, and poly (dimethylmethylenepiperidinium chloride); oil ingredients such as polyhydric alcohol fatty acid esters, polyoxyalkylene polyhydric alcohol fatty acid esters, vegetable fats and oils, animal fats and oils, and mineral oils; higher alcohols such as stearyl alcohol, cholesterol, and phytosterol; higher fatty acids such as myristic acid, palmitic acid, stearic acid, and oleic acid; pearling agents such as ethylene glycol distearates and mica; humectants such as polyhydric alcohols, mucopolysaccharide, hyaluronic acid, chondroitin sulfuric acid, chitosan, ceramide, and cholesterol; thickeners such as methyl cellulose, ethyl cellulose, gum arabic, and polyvinyl alcohol; solvents such as ethanol and 1,3-butylene glycol: antioxidants such as butylhydroxytoluene, tocopherol, and phytic acid; antibacterial and antiseptic agents such as benzoic acid, salicylic acid, sorbic acid, para-hydroxybenzoates, and hexachlorophene; amino acids such as glycine and alanine and salts thereof and organic acids such as citric acid, malic acid, tartaric acid, lactic acid, and naphthalenesulfonic acid and salts thereof; vitamins such as vitamin A and derivatives thereof, vitamin B2 and derivatives thereof, vitamin C and derivatives thereof, vitamin Es, vitamin Ds, vitamin H, pantothenic acid, and pantethine; various drugs such as nicotinic acid amide, benzyl nicotinate, γ-orizanol, allantoin, glycyrrhizinic acid (glycyrrhizinate), and glycyrrhetinic acid and derivatives thereof; natural extracts obtained by extracting *Swertia japonica, Angelica acutiloba,* or *Eucaryptus* with an organic solvents, alcohol, polyhydric alcohol, water or aqueous alcohol; and, in addition, perfumes, scrubbing agents, and purified water.

The hair cleansing composition of the invention can be provided in any form of liquid, emulsion, cream, gel, or foam. The hair cleansing composition of the invention has a pH (at 20° C.) of preferably from 4 to 7.

EXAMPLES

The present invention will hereinafter be described in further detail by Examples. It should however be borne in mind that the invention is not limited to or by them.

In the following preparation examples, examples and comparative examples, all designations of "part", "parts", and "%" mean "part by weight", "parts by weight", or "wt. %", respectively, unless otherwise specifically indicated.

Preparation Example I

Cationic-Group Containing Copolymer

A reaction vessel was charged with an aqueous monomer solution composed of 23.85 g of N,N-dimethylaminoethyl methacrylic acid diethyl sulfate (MOEDES; product of Nitto Kagaku Kogyo K.K.), 71.37 g of N,N-dimethylacrylamide (DMAAm), 0.0429 g of polyethylene glycol dimethacrylate ("NK-9G", product of Shin-Nakamura Chemical), and 350 g of ion exchanged water and purged with nitrogen in advance. After blowing nitrogen into the aqueous solution for 20 minutes, the resulting solution was raised to 55° C. under a nitrogen atmosphere. Then, 0.22 g of (2,2'-azobis(2-amidinopropane)dihydrochloride) was added as a polymerization initiator. Polymerization was started from 30 minutes to 1 hour after the addition to obtain a gel which was entirely soft. Stirring was continued as was. Four hours after the addition of the polymerization initiator, the polymerization was terminated. The content in the form of a sticky rice cake was taken out from the vessel, washed for 10 minutes while stirring in 5 liter of ethanol, and dried. Then it was ground by using a coffee mill and jet mill. The ground particles were then sieved with HI-BOLTER to obtain a KG polymer (0.8 meq/g). The resulting polymer had an average particle size (median particle size based on volume) of 2.7 μm as measured by the above measuring method.

MOEDES:DMAAm:NK-9G=10:90:0.01 (molar ratio), η1:2.5, η2:0.5, ε1:2.4, ε2:1.3, tan δ1:0.98, tan δ2:2.28

Examples 1 to 10, Comparative Examples 1 to 7

The hair cleansing compositions having the composition as shown in Table 4 were prepared in the conventional manner and they were adjusted to pH 6.0 (at 20° C.) with sodium hydroxide. The foam volume, foam quality, and the hair during cleansing and rinsing when they were applied thereto were evaluated as described below with a mean score.

The results are shown collectively in Table 4. The numbers in the table each shows wt. % of a pure content.

Organoleptic evaluation is performed in the following procedure.

A panel of five experts: Japanese women from 25 to 40 years old.

Warm water used: tap water of from 38 to 40° C. (hardness: from 3 to 5° DH)

Procedure:

The experts are each asked to shampoo her hair by pouring warm water and wet her hair, putting an adequate amount (an equal amount to that of a shampoo ordinarily used, depending on the length of her hair) of the hair cleansing composition of the invention on her hands, and moving hands so as to uniformly spread the composition over the hair. The states during shampooing and rinsing are evaluated based on the criteria in the below tables.

The precipitation amount of the complex including Ingredient (D) is determined in the following method.

(Measuring Method)

(1) After 1 g of the shampoo solution (surfactant concentration: 15 wt. %) obtained in each of Examples and Comparative Examples is weighed in a sample tube, 7 g of hard water having water hardness of 4° is added.

(2) A transmittance T (%) at 600 nm is measured (at 20° C.) by using an absorptiometer ("U-2000A", trade name; product of Hitachi, Ltd.).

(3) A turbidity is computed from the transmittance.

Turbidity(%)=100−$T$(%)

TABLE 1

| | Evaluation criteria | | | |
|---|---|---|---|---|
| Score | Foam volume | Foam quality | Tangle free degree during cleansing | Softness of hair during cleansing |
| 5 | Very large foam volume | Fine, very creamy, and good foam quality | No tangles | Very soft to the touch |
| 4 | Large foam volume | Creamy and good foam quality | Almost no tangles | Soft to the touch |

TABLE 1-continued

Evaluation criteria

| Score | Foam volume | Foam quality | Tangle free degree during cleansing | Softness of hair during cleansing |
|---|---|---|---|---|
| 3 | Normal foam volume | Moderately creamy foam quality | Slight tangles | Softish to the touch |
| 2 | Small foam volume | Slightly light and coarse foam quality | Some tangles | Hardish to the touch |
| 1 | Very small foam volume | Light and coarse foam quality | Many tangles | Hard to the touch |

TABLE 2

| Score | Finger combability during rinsing | Softness of the hair during rinsing | Finger combability during wetting | Softness during wetting |
|---|---|---|---|---|
| 5 | Smooth finger combability without no resistance | Very soft to the touch | Smooth finger combability without no resistance | Very soft to the touch |
| 4 | Normal finger combability and no friction between hair strands | Soft to the touch | Normal finger combability and no friction between hair strands | Soft to the touch |
| 3 | Normal finger combability but with some friction between hair strands | Softish to the touch | Normal finger combability but with some friction between hair strands | Softish to the touch |
| 2 | Difficulty in finger combing with friction between hair strands | Hardish to the touch | Difficulty in finger combing with friction between hair strands | Hardish to the touch |
| 1 | No finger combability with strong friction between hair strands | Hard to the touch | No finger combability with strong friction between hair strands | Hard to the touch |

TABLE 3

| Score | Finger combability after drying | Slip of the hair after drying | Softness after drying |
|---|---|---|---|
| 5 | Smooth finger combability without no resistance | Very slippery hair surface | Very soft to the touch |
| 4 | Normal finger combability and no friction between hair strands | Slippery hair surface | Soft to the touch |
| 3 | Normal finger combability but with some friction between hair strands | Slightly slippery hair surface | Softish to the touch |
| 2 | Difficulty in finger combing with friction between hair strands | Not so slippery hair surface | Hardish to the touch |
| 1 | No finger combability with strong friction between hair strands | Not slippery hair surface | Hard to the touch |

TABLE 4

| | Ingredients | Example 1 | 2 | 3 | 4 | 5 | 6 | 7 | 8 | 9 |
|---|---|---|---|---|---|---|---|---|---|---|
| (A) | Sodium polyoxyethylene (10) lauryl ether acetate *1 | 1.5 | 3.75 | 1.88 | | 2.25 | 2.55 | 1.5 | 3.75 | 1.88 |
| | Sodium polyoxyethylene (4.5) lauryl ether acetate *2 | | | | 1.5 | | | | | |
| (B) | Sodium polyoxyethylene (2) lauryl ether sulfate *3 | 6 | 3.75 | 1.88 | 6 | 9 | 10.2 | 6 | 3.75 | 1.88 |
| (C) | Cocamidopropyl betaine *4 | 7.5 | 7.5 | 11.25 | 7.5 | 3.75 | 2.25 | 3.75 | 3.75 | 5.56 |
| | Laurylhydroxysulfobetaine *5 | | | | | | | 3.75 | 3.75 | 5.56 |
| (D) | KG Polymer *6 | 0.3 | 0.3 | 0.3 | 0.3 | 0.3 | 0.3 | 0.3 | 0.3 | 0.3 |
| | Salcare 92 | | | | | | | | | |
| | JR-400 *7 | | | | | | | | | |
| | Salt (NaCl) | 10 | 1.0 | 1.0 | 1.0 | 1.0 | 1.0 | 1.0 | 1.0 | 1.0 |
| | Purified water | Balance | Balance | Balance | Balance | Balance | Balance | Balance | Balance | Balance |
| | Foam volume | 4 | 3.75 | 3.75 | 4 | 4 | 4 | 4 | 4.25 | 4.5 |
| | Foam quality (creamy foam) | 4 | 4.5 | 4 | 4.5 | 4 | 4 | 4 | 4.5 | 4.25 |
| | Tangle-free hair during cleansing | 4.25 | 4.25 | 4.25 | 4 | 4 | 4 | 4.25 | 4.5 | 4.25 |
| | Softness during cleansing | 3.75 | 4.5 | 4 | 4.5 | 4.25 | 3.75 | 4 | 4.5 | 4 |
| | Finger combability during rinsing | 4 | 4.5 | 4 | 3.75 | 4.25 | 4 | 4 | 4.5 | 4.5 |
| | Softness during rinsing | 4.5 | 4.5 | 4 | 4 | 4 | 4 | 4.5 | 4.5 | 4.5 |

TABLE 4-continued

| | | | | | | | | | |
|---|---|---|---|---|---|---|---|---|---|
| Turbidity (%) | 38.28 | 38.48 | 34.35 | 38.06 | 11.3 | 8.47 | — | — | — |
| A/C | 0.2 | 0.5 | 0.17 | 0.2 | 0.6 | 1.13 | 0.2 | 0.5 | 0.17 |
| A/B | 0.25 | 1 | 1 | 0.25 | 0.25 | 0.25 | 0.25 | 1 | 1 |
| B/C | 0.8 | 0.5 | 0.17 | 0.8 | 2.4 | 4.53 | 0.8 | 0.5 | 0.17 |
| A/(A + B + C) | 0.1 | 0.25 | 0.13 | 0.1 | 0.15 | 0.17 | 0.1 | 0.25 | 0.13 |
| D/A | 0.2 | 0.08 | 0.16 | 0.2 | 0.13 | 0.12 | 0.2 | 0.08 | 0.16 |

| | | Example | Comparative Example | | | | | | |
|---|---|---|---|---|---|---|---|---|---|
| Ingredients | | 10 | 1 | 2 | 3 | 4 | 5 | 6 | 7 |
| (A) Sodium polyoxyethylene (10) lauryl ether acetate *1 | | 2.25 | | 7.5 | 7.5 | 3.75 | | | |
| Sodium polyoxyethylene (4.5) lauryl ether acetate *2 | | | | | | | 8.82 | 1.5 | 1.5 |
| (B) Sodium polyoxyethylene (2) lauryl ether sulfate *3 | | 9 | 12.75 | 7.5 | | | 4.41 | 6 | 6 |
| (C) Cocamidopropyl betaine *4 | | 1.87 | 2.25 | | 7.5 | 11.25 | 1.76 | 7.5 | 7.5 |
| Laurylhydroxysulfobetaine *5 | | 1.87 | | | | | | | |
| (D) KG Polymer *6 | | 0.3 | 0.3 | 0.3 | 0.3 | 0.3 | 0.3 | | |
| Salcare 92 | | | | | | | | 0.3 | |
| JR-400 *7 | | | | | | | | | 0.3 |
| Salt (NaCl) | | 1.0 | 1.0 | 1.0 | 1.0 | 1.0 | 1.0 | 1.0 | 1.0 |
| Purified water | | Balance | Balance | Balance | Balance | Balance | Balance | Balance | Balance |
| Foam volume | | 4.5 | 4 | 3.5 | 2.5 | 2 | 2 | 4 | 4.25 |
| Foam quality (creamy foam) | | 4.5 | 4 | 3 | 3 | 2.5 | 2.5 | 3.5 | 3.5 |
| Tangle-free hair during cleansing | | 4 | 3.75 | 3.5 | 2.5 | 2 | 2.5 | 3 | 3 |
| Softness during cleansing | | 4.5 | 3.5 | 3.5 | 3.75 | 3.5 | 3.5 | 2.5 | 2.5 |
| Finger combability during rinsing | | 4.5 | 2.5 | 2.5 | 4.5 | 4.5 | 4 | 1 | 1.5 |
| Softness during rinsing | | 4 | 2.5 | 3 | 4.5 | 4.5 | 4 | 1.5 | 1.5 |
| Turbidity (%) | | — | 5.43 | 6.91 | 15.62 | 4.49 | 13.77 | — | — |
| A/C | | 0.60 | 0 | | 1 | 0.33 | 5.01 | 0.2 | 0.2 |
| A/B | | 0.25 | 0 | 1 | — | — | 2 | 0.25 | 0.25 |
| B/C | | 2.41 | 5.67 | — | 0 | 0 | 2.51 | 0.8 | 0.8 |
| A/(A + B + C) | | 0.15 | 0 | 0.5 | 0.5 | 0.25 | 0.59 | 0.1 | 0.1 |
| D/A | | 0.13 | — | 0.04 | 0.04 | 0.08 | 0.03 | — | — |

The following are surfactants and polymers used in Table 4. The number in this table indicates a pure content. A total amount of the pure contents of the surfactants is set at 15 wt. %.
*1: "KAO AKYPO RLM100NV" (trade name; product of Kao)
*2: "KAO AKYPO RLM45NV" (trade name; product of Kao)
*3: "EMAL 270J" (trade name; product of Kao)
*4: "AMPHITOL 55AB" (trade name; product of Kao)
*5: "AMPHITOL 20HD" (trade name; product of Kao)
*6: The above polymer particles
*7: "JR-400 INCI: Polyquaternium-10" product of Dow Amerchol
"Salcare 92": Crosslinked polymer of acrylamide/methacryloyloxyethyltrimethylammonium chloride (20/80), product of Ciba, 3.8 meq/g
The term "purified water" as used herein means ion exchanged water.

Table 4 has revealed that the cleansing agents according to the invention are superior to those obtained in Comparative Examples in finger combability and softness during cleansing and rinsing while providing satisfactory foam quality and foam volume. The complex precipitated during the dilution procedure of the cleansing agent of the invention is presumed to give such a sensation.

Comparison between Example 4 and Comparative Examples 6 and 7 has revealed that the cleansing compositions using a cationic polymer are inferior in performance when the polymer is different from that of the invention. It is apparent from the results of Example 7 to Example 10 that the cleansing composition containing both cocamidopropyl betaine (carbobetaine) and laurylhydroxysulfobetaine (sulfobetaine) in combination has both an improved foam performance and an improved hair feel.

Example 11, Comparative Examples 8 to 9

The hair cleansing compositions having the composition shown in Table 5 were prepared in the conventional manner and they were adjusted to pH 6.0 (at 20° C.) with sodium hydroxide. Their foam volume, foam quality and the hair during wetting or after drying, in addition to the hair during cleansing and rinsing were evaluated similarly with a mean score.

The precipitation amount of silicone is determined by the following method.
(Measuring Method)
(1) A hair bundle (1 g, 10 cm) made of the hair of Asian people is foamed with 1.6 g of an eight-fold diluted shampoo solution for 30 seconds.
(2) The hair bundle is rinsed three times with 500 ml of warm water of 40° C. Described specifically, rinsing contains immersing of the hair bundle in warm water and then pulling it up therefrom, each five times.
(3) The hair bundle is blow dried.
(4) The hair bundle thus treated is placed in a test tube and 5 ml of chloroform is added thereto. The test tube is agitated for 30 seconds, followed by transfer to an Erlenmeyer flask (repeated three times).
(5) To the flask is added 5 ml of 200 ppm of dinitrobenzene as an internal standard (chloroform solution).
(6) The resulting mixture is evaporated to dryness with a nitrogen gas.
(7) The Erlenmeyer flask is washed with 1 ml of chloroform and 1H of the content in an NMR tube is measured.
(8) From the peak intensities (below) of the internal standard and silicone obtained from the measurement results, the residual amount of silicone is determined using NMR.
$^1$H-NMR spectrum
0.05-0.25 ppm (Si—$CH_3$)

TABLE 5

|  | Ingredients | Example 11 | Comparative Example 8 | Comparative Example 9 |
|---|---|---|---|---|
| (A) | Sodium polyoxyethylene (10) lauryl ether acetate *1 | | | |
|  | Sodium Polyoxyethylene (4.5) lauryl ether acetate *2 | 1.5 | 1.5 | 1.5 |
| (B) | Sodium polyoxyethylene (2) lauryl ether sulfate *3 | 6 | 6 | 6 |
| (C) | Cocamidopropyl betaine | 7.5 | 7.5 | 7.5 |
| (D) | KG Polymer *4 | 0.3 | | |
|  | Ciba Salcare 92 | | 0.3 | |
|  | JR-400 *5 | | | 0.3 |
| (E) | Silicone *6 | 1.8 | 1.8 | 1.8 |
|  | Salt (NaCl) | 1.0 | 1.0 | 1.0 |
|  | Cetyl alcohol *7 | 0.5 | 0.5 | 0.5 |
|  | Pearling agent *8 | 0.5 | 0.5 | 0.5 |
|  | Purified water | Balance | Balance | Balance |
| Foam volume | | 3.5 | 3.5 | 3.5 |
| Foam quality (creamy foam) | | 4 | 3.5 | 4 |
| Tangle-free hair during cleansing | | 4 | 2 | 3.5 |
| Softness during cleansing | | 4 | 1.5 | 3.5 |
| Finger combability during rinsing | | 4 | 2.5 | 2 |
| Softness during rinsing | | 4 | 2 | 2.5 |
| Finger combability during wetting | | 3.75 | 2 | 1.5 |
| Softness during wetting | | 4 | 1.5 | 2.5 |
| Finger combability after drying | | 3.25 | 2.5 | 2.5 |
| Slip after drying | | 4 | 3.5 | 2.5 |
| Softness after drying | | 3.5 | 3 | 3 |
| Residual amount of Silicone (μg/g-hair) | | 816.82 | 207.76 | 170.19 |
| A/C | | 0.20 | 0.20 | 0.20 |
| A/B | | 0.25 | 0.25 | 0.25 |
| B/C | | 0.8 | 0.8 | 0.8 |
| A/(A + B + C) | | 0.1 | 0.1 | 0.1 |
| D/A | | 0.2 | — | — |
| D/E | | 0.17 | — | — |

The following are the surfactants and polymers used in Table 5. The number in the table indicates wt. % of a pure content.
*1: "KAO AKYPO RLM100NV" (trade name; product of Kao)
*2: "KAO AKYPO RLM45NV" (trade name; product of Kao)
*3: "EMAL 270J" (trade name; product of Kao)
*4: The above polymer particles
*5: "JR-400" (trade name; product of Dow Amerchol)
*6: "BY22-050A" (trade name; product of Dow Corning Toray)
*7: "KALCOL6098" (trade name; product of Kao)
*8: Ethylene glycol distearate The results in Table 5 have revealed that the composition obtained in Example 11 is superior to those obtained in Comparative Examples 8 and 9 in slip, softness, and finger combability during wetting or after drying. The superiority of the composition of Example 11 is presumed to result from an increase in the residual amount of silicone through the action of the complex. A hair cleansing composition was prepared in a similar manner to Example 11 except that cocamidopropylbetaine was replaced by cocamidopropyl betaine and lauryl hydroxysulfobetaine which were used at a weight ratio of 1/1. The resulting composition had an improved foam performance and an improved hair sensation.

The invention claimed is:

1. A method for cleansing hair, comprising contacting hair with a hair cleansing composition comprising ingredients (A), (B), (C), and (D) at a weight ratio of (A) to (B) [(A)/(B)] of from 0.1 to 1.2, at a weight ratio of (A) to (C) [(A)/(C)] of from 0.1 to 1.2, at a weight ratio of (D) to the total weight of (A), (B), and (C) [(D)/((A)+(B)+(C))] of from 0.005 to 0.1, and at a total weight of (A), (B), and (C) [(A)+(B)+(C)] of from 5 to 30 wt %:

(A) 1 to 8 wt. % of an ether carboxylate surfactant of formula (4):

$$R^{11}-Z^1-(A^1O)_n-Y^1-COOX^1 \qquad (4)$$

wherein $R^{11}$ represents an alkyl or alkenyl group which may contain a linear or branched hydroxyl group having from 12 to 16 carbon atoms, $Z^1$ represents —O—, $A^1$ represents an alkylene group having 2 carbon atoms, $X^1$ represents a hydrogen atom, an alkali metal, an alkaline earth metal, ammonium, or an organic ammonium, $Y^1$ represents an alkylene group having from 1 to 3 carbon atoms, and n stands for an average addition molar number and is from 4 to 10, (B) 1 to 15 wt. % of an ether sulfate surfactant of formula (6):

$$R^{13}O(CH_2CH_2O)_pSO_3M^2 \qquad (6)$$

wherein $R^{13}$ represents an alkyl or alkenyl group having from 10 to 18 carbon atoms, p means an average addition molar number and is from 0.5 to 3, and $M^2$ represents a hydrogen atom, an alkali metal, an alkaline earth metal, ammonium, or an organic ammonium, (C) 2 to 15 wt. % of one or more betaine amphoteric surfactant selected from the group consisting of carbobetaine and sulfobetaine, and (D) 0.01 to 3 wt % of a cationic-group containing copolymer obtained by the copolymerization of a monomer mixture containing the following monomers (a1), (a2), and (a3):

(a1) at least one hydrophilic nonionic-group containing vinyl monomer of formula (I):

(I)

wherein $R^1$ represents a hydrogen atom or a methyl group, $R^2$ represents a hydrogen atom or a linear alkyl group having from 1 to 4 carbon atoms, and $R^3$ represents a linear alkyl group having from 1 to 4 carbon atoms;

(a2) at least one cationic-group containing vinyl monomer of formula (III):

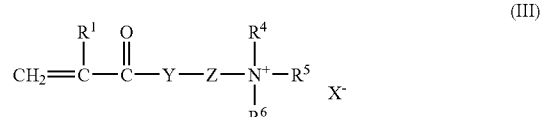

(III)

wherein $R^1$ has the same meaning as described above, $R^4$ and $R^5$ are the same or different and each represents an alkyl group having from 1 to 4 carbon atoms, $R^6$ represents a hydrogen atom or an alkyl group having from 1 to 4 carbon atoms, Y represents a group —O—, Z represents a linear or branched alkylene group having from 1 to 4 carbon atoms, and X is an alkyl sulfate group having from 1 to 4 carbon atoms;

and (a3) a crosslinkable monomer having two or more reactive unsaturated groups, wherein the molar ratio of (a1)/(a2) ranges from 60/40 to 93/7, and wherein (a3) is present in an amount of from 0.002 to 0.08 wt % based on the total amount of monomers.

2. The method according to claim 1, wherein a weight ratio of a content of (A) to a total content of (A), (B), and (C) [(A)/[(A)+(B)+(C)] falls within a range of from 0.08 to 0.37.

3. The method according to claim 1, wherein a weight ratio of a content of (D) to a content of (A) [(D)/(A)] falls within a range of from 0.05 to 0.3.

4. The method according to claim 1, wherein (D) is polymer particles.

5. The method according to claim 1, wherein (C) comprises carbobetaine and sulfobetaine.

6. The method according to claim 5, wherein a weight ratio of carbobetaine to sulfobetaine (carbobetaine/sulfobetaine) falls within a range of from 1/5 to 5/1.

7. The method according to claim 1, having a turbidity of 10% or greater as determined in accordance with equation (1) from a transmittance T (%) (600 nm) of a cleansing composition:

Turbidity (%)=100−T(%)  (1)

wherein said cleaning composition is prepared by a method comprising:
preparing a cleansing composition to give a total content of (A) to (C) of 15 wt. % while keeping the composition ratio of (A) to (D), with the proviso that the cleansing composition contains, as ingredients other than (A) to (D), only 1 wt. % of NaCl, purified water, and if necessary, a pH regulator and has a pH (at 20° C.) adjusted to 6.0, and
diluting 1 g of the cleansing composition obtained in said preparing with 7 g of hard water having water hardness of 4°, and wherein said turbidity is measured upon said diluting.

8. The method according to claim 1, further comprising silicone as (E).

9. The method according to claim 8, wherein a weight ratio of the cationic-group containing copolymer as (D) to the silicone as (E) [(D)/(E)] falls within a range of from 1/20 to 1/1.

10. A method for cleansing hair, comprising contacting hair with a hair cleansing composition comprising a surfactant and ingredient (D), wherein the surfactant in said hair cleansing composition consists essentially of ingredients (A), (B) and (C), wherein (A) and (B) are present in a weight ratio of (A) to (B) [(A)/(B)] of from 0.1 to 1.2, wherein (A) and (C) are present in a weight ratio of (A) to (C) [(A)/(C)] of from 0.1 to 1.2, at a weight ratio of (D) to the total weight of (A), (B), and (C) [(D)/((A)+(B)+(C))] of from 0.005 to 0.1, and at a total weight of (A), (B), and (C) [(A)+(B)+(C)] of from 5 to 30 wt %:

(A) 1 to 8 wt. % of an ether carboxylate surfactant represented by the following formula (4):

$R^{11}-Z^1-(A^1O)_n-Y-COOX^1$  (4)

wherein $R^{11}$ represents an alkyl or alkenyl group which may contain a linear or branched hydroxyl group having from 12 to 16 carbon atoms, $Z^1$ represents —O—, $A^1$ represents an alkylene group having 2 carbon atoms, $X^1$ represents a hydrogen atom, an alkali metal, an alkaline earth metal, ammonium, or an organic ammonium, $Y^1$ represents an alkylene group having from 1 to 3 carbon atoms, and n stands for an average addition molar number and is from 4 to 10, (B) 1 to 15 wt. % of an ether sulfate surfactant represented by the following formula (6):

$R^{13}O(CH_2CH_2O)_pSO_3M^2$  (6)

wherein $R^{13}$ represents an alkyl or alkenyl group having from 10 to 18 carbon atoms, p means an average addition molar number and is from 0.5 to 3, and $M^2$ represents a hydrogen atom, an alkali metal, an alkaline earth metal, ammonium, or an organic ammonium, (C) 2 to 15 wt. % of one or more betaine amphoteric surfactant selected from the group consisting of carbobetaine and sulfobetaine, and (D) 0.01 to 3 wt % of a cationic-group containing copolymer obtained by the copolymerization of a monomer mixture containing the following Monomers (a1), (a2), and (a3):

(a1) at least one hydrophilic nonionic-group containing vinyl monomer of formula (I):

wherein $R^1$ represents a hydrogen atom or a methyl group, $R^2$ represents a hydrogen atom or a linear alkyl group having from 1 to 4 carbon atoms, and $R^3$ represents a linear alkyl group having from 1 to 4 carbon atoms;

(a2) at least one cationic-group containing vinyl monomer of formula (III):

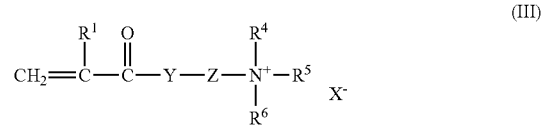

wherein $R^1$ has the same meaning as described above, $R^4$ and $R^5$ are the same or different and each represents an alkyl group having from 1 to 4 carbon atoms, $R^6$ represents a hydrogen atom or an alkyl group having from 1 to 4 carbon atoms, Y represents a group —O—, Z represents a linear or branched alkylene group having from 1 to 4 carbon atoms, and X is an alkyl sulfate group having from 1 to 4 carbon atoms;

and (a3) a crosslinkable monomer having two or more reactive unsaturated groups, wherein the molar ratio of (a1)/(a2) ranges from 60/40 to 93/7, and wherein (a3) is present in an amount of from 0.002 to 0.08 wt % based on the total amount of monomers.

11. The method according to claim 10, wherein a weight ratio of a content of (A) to a total content of (A), (B), and (C) [(A)/[(A)+(B)+(C)] falls within a range of from 0.08 to 0.37.

12. The method according to claim 10, wherein a weight ratio of a content of (D) to a content of (A) [(D)/(A)] falls within a range of from 0.05 to 0.3.

13. The method according to claim 10, wherein (D) is polymer particles.

14. The method according to claim 10, wherein (C) comprises carbobetaine and sulfobetaine.

15. The method according to claim 14, wherein a weight ratio of carbobetaine to sulfobetaine (carbobetaine/sulfobetaine) falls within a range of from 1/5 to 5/1.

16. The method according to claim 10, having a turbidity of 10% or greater as determined in accordance with equation (1) from a transmittance T (%) (600 nm) of a cleansing composition:

Turbidity (%)=100−T (%)  (1)

wherein said cleaning composition is prepared by a method comprising:

preparing a cleansing composition to give a total content of (A) to (C) of 15 wt. % while keeping the composition ratio of (A) to (D), with the proviso that the cleansing composition contains, as ingredients other than (A) to (D), only 1 wt. % of NaCl, purified water, and if necessary, a pH regulator and has a pH (at 20° C.) adjusted to 6.0, and diluting 1 g of the cleansing composition obtained in said preparing with 7 g of hard water having water hardness of 4°, and wherein said turbidity is measured upon said diluting.

17. The method according to claim 10, further comprising silicone as (E).

18. The method according to claim 17, wherein a weight ratio of the cationic-group containing copolymer as (D) to the silicone as (E) [(D)/(E)] falls within a range of from 1/20 to 1/1.

* * * * *

UNITED STATES PATENT AND TRADEMARK OFFICE
CERTIFICATE OF CORRECTION

PATENT NO.         : 8,741,825 B2
APPLICATION NO.    : 12/863998
DATED              : June 3, 2014
INVENTOR(S)        : Tomoko Uchiyama et al.

Page 1 of 1

It is certified that error appears in the above-identified patent and that said Letters Patent is hereby corrected as shown below:

In the Claims

At Column 21, delete line 51 in its entirety and replace with the following:

-- $R^{11}\text{-}Z^{1}\text{-}(A^{1}O)_{n}\text{-}Y^{1}\text{-}COOX^{1}$ --

Signed and Sealed this
Sixteenth Day of September, 2014

Michelle K. Lee
*Deputy Director of the United States Patent and Trademark Office*